United States Patent [19]

Hatano et al.

[11] Patent Number: 5,049,692

[45] Date of Patent: Sep. 17, 1991

[54] CATALYTIC CONVERSION OF ALKANES TO NITRILES, AND A CATALYST THEREFOR

[75] Inventors: Masakatsu Hatano; Atsushi Kayo, both of Yokohama, Japan

[73] Assignee: Mitsubishi Kasei Corporation, Tokyo, Japan

[21] Appl. No.: 515,687

[22] Filed: Apr. 26, 1990

Related U.S. Application Data

[63] Continuation of Ser. No. 273,924, Nov. 21, 1988, abandoned.

[30] Foreign Application Priority Data

Nov. 25, 1987 [JP] Japan ................................. 62-295054
Feb. 18, 1988 [JP] Japan ..................................... 63-3399
Aug. 9, 1988 [JP] Japan .............................. 63-197126

[51] Int. Cl.$^5$ ......................................... C07C 253/24
[52] U.S. Cl. ..................................... 558/319; 558/318
[58] Field of Search ............................... 558/319, 318

[56] References Cited

U.S. PATENT DOCUMENTS

| | | | |
|---|---|---|---|
| 3,433,823 | 3/1969 | McMahon | 558/319 X |
| 3,670,008 | 6/1972 | Taylor | 260/465.3 |
| 3,686,267 | 8/1972 | Taylor | 260/465.3 |
| 3,833,638 | 9/1974 | Knox et al. | 558/319 |
| 3,860,534 | 1/1975 | Harris et al. | 558/319 X |
| 3,936,505 | 2/1976 | Oda et al. | 568/479 X |
| 4,025,565 | 5/1977 | Oda et al. | 568/479 X |
| 4,609,502 | 9/1986 | Khoobtar et al. | 558/320 |
| 4,736,054 | 4/1988 | Attig et al. | 558/319 |
| 4,746,641 | 5/1988 | Guttmann et al. | 502/202 |
| 4,760,159 | 7/1988 | Suresh et al. | 558/319 |
| 4,767,739 | 8/1988 | Glaeser et al. | 502/209 |

FOREIGN PATENT DOCUMENTS

| | | |
|---|---|---|
| 901005 | 5/1972 | Canada . |
| 282314 | 9/1988 | European Pat. Off. . |
| 2173203 | 10/1973 | France . |
| 1194855 | 6/1970 | United Kingdom . |
| 1334859 | 10/1973 | United Kingdom . |
| 2090156 | 7/1982 | United Kingdom . |

*Primary Examiner*—Joseph Paul Brust
*Attorney, Agent, or Firm*—Oblon, Spivak, McClelland, Maier & Neustadt

[57] ABSTRACT

Disclosed herein is a process for producing a nitrile which comprises subjecting an alkane to a gas-phase catalytic oxidation reaction with ammonia in the presence of a complex oxide solid catalyst composed of molybdenum, vanadium, tellurium and niobium.

According to the process of the present invention, it is possible to produce the objective nitrile at a high selectivity without using a halide, water, etc., moreover, at a relatively low temperature of about 350° to 480° C., particularly about 400° to 450° C.

2 Claims, No Drawings

CATALYTIC CONVERSION OF ALKANES TO NITRILES, AND A CATALYST THEREFOR

This application is a continuation of application Ser. No. 07/273,924, filed on Nov. 21, 1988, now abandoned.

BACKGROUND OF THE INVENTION

The present invention relates to a process for producing nitriles. More particularly, it relates to an improved method for producing nitriles by using an alkane as starting material.

Nitriles such as acrylonitrile and methacrylonitrile have been industrially produced as an important intermediate for the preparation of fibers, synthetic resins, synthetic rubbers and the like. The most popular method for producing such nitriles is to subject an olefin such as propylene, isobutene or the like to a catalytic reaction with ammonia and oxygen in the presence of a catalyst in a gaseous phase at a high temperature.

More recently, there have been proposed methods for producing acrylonitrile or methacrylonitrile by using the so-called ammoxidation process, according to which a lower alkane such as propane, isobutane, etc., is subjected to a catalytic reaction with ammonia and oxygen in the presence of a catalyst in a gaseous phase. For instance, a method using an Mo type catalyst (Japanese Patent Application Laid-Open (KOKAI) Nos. 48-16887 (1973), 47-13312 (1972) (corresponding to GB 1,333,639), and 47-13313 (1972) (corresponding to USP 3,833,638) and Japanese Patent Publication No. 55-42071 (1980)), a method using V type catalyst (Jpn. Pat. Appln. Laid-Open (KOKAI) Nos. 47-33783 (1972) and 52-148022 (1977), Jpn. Pat. Pub. Nos. 50-23016 (1975) (corresponding to GB 1,336,135 and GB 1,336,136) and 47-51331 (1972) (corresponding to USP 3,433,823)), a method using Sb type catalyst (Jpn. Pat. Pub. Nos. 45-4733 (1970) (corresponding to GB 1,194,855), 47-14371 (1972) (corresponding to USP 3,670,008, USP 3,678,090 and USP 3,816,506), 50-17046 (1975) (corresponding to USP 3,670,006, USP 3,686,267 and USP 3,743,527), 50-28940 (1975) (corresponding to GB 1,334,859), 56-47901 (1981), and USP 3,686,295), and a method using other types of catalyst (Jpn. Pat. Pub. No. 50-16775 (1975) (corresponding ,to USP 3,652,638)) are known, but none of these known methods is satisfactory in selectivity of the objective nitriles.

In order to improve the selectivity of nitriles, it has been attempted to add a small quantity of an organic halide, inorganic halide or sulfur compound to the reaction system or to add water to the reaction system. However, the former method has a problem of possible corrosion of a reaction apparatus while the latter method involves a problem of formation of by-products by a side reaction.

Further, the methods using the conventional catalysts require a very high reaction temperature, which is about 500° C. or higher, so that such methods are disadvantageous in terms of reactor material, production cost, etc.

The present inventors have made extensive researches on the method of producing nitriles by using an alkane as starting material and, as a result, found that by using a specific complex catalyst it was possible to produce the objective nitriles with a higher selectivity than attainable with the conventional methods, with no need of introducing a halide or water into the reaction system and at a lower temperature (about 380 to 480° C.) than required in the conventional methods. The present invention was attained on the basis of such finding.

SUMMARY OF THE INVENTION

In an aspect of the present invention, there is provided a process for producing nitriles which comprises subjecting an alkane to a gas-phase catalytic oxidation reaction with ammonia in the presence of a complex oxide solid catalyst composed of molybdenum, vanadium, tellurium and niobium.

DETAILED DESCRIPTION OF THE INVENTION

The feature of the present invention lies in using a complex oxide solid catalyst containing molybdenum (Mo), vanadium (V), tellurium (Te) and niobium (Nb) as essential components in the ammoxidation of alkane. Typical examples of such complex oxide solid catalyst are those represented by the following empirical formula:

$$Mo_{1.0}V_aTe_bNb_cO_x$$

wherein a, b and c represent atomic ratios of the respective component elements based on Mo, a being 0.01 to 1.0, b being 0.01 to 0.5 and c being 0.01 to 1.0, and x is a number decided by the total number of valencies of the metal elements.

These catalysts can be prepared in the following way for instance. Into an aqueous solution containing a given amount of ammonium metavanadate are added successively an aqueous solution of ammonium niobium oxalate, an aqueous solution of telluric acid and an aqueous solution of ammonium paramolybdate in such amounts that the atomic ratios of the respective metal elements would fall in the range specified above, and the mixture is heated and concentrated at about 70° C. for about 30 minutes and then evaporated to dryness at 130° C. The resulting dry solid is calcined at a high temperature of from 350 to 650° C., preferably 350 to 450° C., for about 3 hours to give a desired catalyst.

In the above preparation process, the order of addition of the respective metal elements—molybdenum, vanadium, tellurium and niobium—is not specified, but it is desirable to add the molybdenum component, for example, an aqueous solution of ammonium paramolybdate, last of all as it faciliates obtaining a uniform aqueous solution.

In the above preparation, ammonium metavanadate may be replaced by $V_2O_5$, $V_2O_3$, $VOCl_3$, $VCl_4$ or the like. Ammonium niobium oxalate may be replaced by $NbCl_3$, $NbCl_5$, $Nb_2(C_2O_4)_5$ or the like. Also, telluric acid may be replaced by $TeO_2$ or the like, and ammonium paramolybdate may be replaced by $MoO_3$, $MoCl_5$, phosphomolybdic acid, silicomolybdic acid or the like. It is also possible to use a heteropolyacid which contains mixed-coordinate molybdenum and vanadium, such as molybdovanadophoaphoric acid.

The contents of said metal elements constituting the catalyst used in the present invention are selected such that the ratio of vanadium to one atom of molybdenum will be 0.01 to 1.0 atom, preferably 0.2 to 0.4 atom, the ratio of tellurium to one atom of molybdenum will be 0.01 to 0.5 atom, preferably 0.2 to 0.4 atom, and the ratio of niobium to one atom of molybdenum will be 0.01 to 1.0 atom, preferably 0.1 to 0.2 atom.

Such catalyst may be used either singly or in combination with a known carrier such as silica, alumina, aluminosilicate and the like. The catalyst is worked into a suitable particle diameter and shape according to the scale and system of the reaction and/or other factors in the manner commonly practiced in the art.

The process of the present invention is a process for producing nitriles by subjecting alkanes to a gas-phase catalytic oxidation reaction with ammonia in the presence of the catalyst specified above.

As the alkane of the starting material, it is not particularly limited and for instance, alkanes of 1 to 7 carbon atoms such as methane, ethane, propane, butane, isobutane, pentane, hexane, heptane, etc. may be mentioned, however, in consideration of the industrial use of the nitrile to be produced, it is preferable to use a lower alkane of 1 to 4 carbon atoms. Further, the oxidation reaction of the process of the present invention is carried out by the oxygen atoms existing in the catalyst or by the molecular oxygen which is supplied with the starting material gas.

In the case where molecular oxygen is supplied with the starting material, although pure oxygen gas may be used, since the purity of oxygen gas is not required, it is economical to use a molecular oxygen-containing gas such as air. In the case where molecular oxygen is not contained in the supplied gas as the starting material, it is preferable to alternately supply a gaseous mixture of alkane and ammonia and a molecular oxygen-containing gas to prevent the reductive deterioration of the catalyst, or to transfer used catalysts continuously into an ordinary oxydative regenerator to use the thus regenerated catalyst while using a reactor of moving bed type.

As the reactor used in the process according to the present invention, any one of the reactors hitherto used in a gas phase contact catalytic reaction may be used, and further, the introduction and the extraction of the catalyst may be carried out as in the conventional process. The catalyst is usually used in an amount of 0.02 to 2.4 cc, preferably 0.1 to 0.5 cc to one mole per hour of the supplied alkane.

Alkane, ammonia, the optional molecular oxygen-containing gas and a diluent gas optionally used for regulating the space velocity and the partial pressure of oxygen may be supplied individually to the reactor, however, it is preferable to mix these substances in advance and then to supply the thus prepared gaseous mixture to the reactor.

The amount of ammonia used in the reaction is 0.5 to 3 mol, preferably 0.8 to 1.5 mol per one mol of alkane.

The amount of the molecular oxygen-containing gas which is used in the case of necessity is important concerning the selectivity of the nitriles, and the molecular oxygen-containing gas is used so that the amount of molecular oxygen is not more than 5 mol, preferably 1 to 3 mol, more preferably 1 to 1.6 mol per one mol of alkane.

As the diluent gas, an inactive gas such as nitrogen, argon, helium, etc. may be used. By increasing and decreasing the amount used of the diluent gas in the above-mentioned range, it is possible to regulate the space velocity and the partial pressure of oxygen in the supplied gas into a suitable range.

The space velocity of the supplied gas (a mixture of alkane, ammonia, the molecular oxygen-containing gas optionally used and the diluent gas optionally used) is 100 to 10,000 $hr^{-1}$, preferably 500 to 2,000 $hr^{-1}$.

In the present invention, the gas phase contact reaction of alkane and ammonia is carried out at a temperature which is lower than the temperature of the conventional ammoxydation, namely 380 to 480° C., preferably 400 to 450° C. under atmospheric pressure, a slightly increased pressure or a slightly reduced pressure.

In the case where the ammoxidation reaction of alkane is carried out according to the process of the present invention, for instance, an $\alpha,\beta$-unsaturated nitrile such as methacrylonitrile, acrylonitrile, etc. is formed from isobutane and propane, acetonitrile is formed from ethane and hydrogen cyanide is formed from methane. In addition to these compounds, carbon monoxide, carbon dioxide, nitriles other than the objective nitrile, etc. are by-produced, however, the amount of production of the by-products is remarkably small.

Further, the separation of the objective nitrile from the reaction mixture and the purification of the thus separated nitrile can be carried out while following the conventional method.

The present invention will be explained more in detail while referring to the following non-limitative Examples.

Further, the conversion (%) of an alkane and the selectivity(%) of a nitrile in Examples and Comparative Examples are respectively shown by the following formulae:

$$\text{Conversion of alkane}(\%) = \frac{\text{mols of consumed alkane}}{\text{mols of supplied alkane}} \times 100$$

$$\text{Selectivity of objective nitrile}(\%) = \frac{\text{mols of objective nitrile obtained}}{\text{mols of consumed alkane}} \times 100$$

REFERENCE EXAMPLE 1 (Preparation of the catalyst)

Into 100 ml of warm water, 1170 mg of ammonium metavanadate were dissolved, and into the thus formed solution, 12.5 ml of an aqueous solution of ammonium niobium oxalate (0.2 Nb atom/litre), 10.0 ml of an aqueous solution of telluric acid (0.5 Te atom/litre) and 25.0 ml of an aqueous solution of ammonium paramolybdate (1.0 Mo atom/liter) were added to prepare a uniform aqueous solution.

After heating the thus prepared aqueous solution, it was evaporated to dryness in a drier at 130° C. to obtain a solid material.

The thus obtained solid material was calcined at 350° under a flow of air, and after molding the calcined material into a tablet of a size of 5 mm in diameter and 3 mm in length using a tablet machine, the tablet was pulverized and sifted into a powder of 16 to 28 mesh. The empirical formula of the thus prepared catalyst was as follows:

$Mo_{1.0}V_{0.4}Te_{0.2}Nb_{0.1}O_{4.65}$

REFERENCE EXAMPLE 2 (Preparation of the catalyst)

In the same manner as in Reference Example 1 except for changing the amount of telluric acid, the following two kinds of the catalyst were obtained:

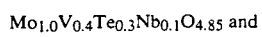

$Mo_{1.0}V_{0.4}Te_{0.3}Nb_{0.1}O_{4.85}$ and $Mo_{1.0}V_{0.4}Te_{0.4}Nb_{0.1}O_{5.05}$

EXAMPLES 1 to 4

After charging a reactor with 0.5 cc of the catalyst obtained in Reference Example 1, a gaseous mixture of propane, ammonia, air and nitrogen in a molar ratio shown in Table 1 was supplied into the reactor at a space velocity of 1400 hr$^{-1}$ to carry out the gas phase catalytic reaction at 422° C. The results are shown in Table 1.

TABLE 1

| Example | Composition of gas (molar ratio) | | | | Conversion of propane (%) | Selectivity of acrylonitrile (%) |
|---|---|---|---|---|---|---|
| | Propane | NH$_3$ | Air | N$_2$ | | |
| 1 | 1 | 1.2 | 12.4 | 2.4 | 24.4 | 51.8 |
| 2 | 1 | 1.2 | 10.4 | 4.9 | 22.6 | 61.5 |
| 3 | 1 | 1.2 | 7.6 | 7.3 | 20.9 | 71.6 |
| 4 | 1 | 1.2 | 5.1 | 9.8 | 11.0 | 78.4 |

COMPARATIVE EXAMPLE 1

While using a catalyst of the atomic ratio shown in Table 2 prepared in the same manner as in Reference Example 1 except for not using the Nb component, a gaseous mixture of propane, ammonia, air and nitrogen of the same composition as in Example 1 was supplied into a reactor at the same space velocity as in Example 1 to carry out the reaction at the temperature shown in Table 2. The results are shown in Table 2.

COMPARATIVE EXAMPLE 2

While using a catalyst of the atomic ratio shown in Table 2 prepared in the same manner as in Reference Example 1 except for not using the Te component, a gaseous mixture of propane, ammonia, air and nitrogen of the same composition as in Example 1 was supplied into a reactor at the same space velocity as in Example 1 to carry out the reaction at the temperature shown in Table 2. The results are shown in Table 2.

COMPARATIVE EXAMPLE 3

While using a catalyst of the atomic ratio shown in Table 2 prepared in the same manner as in Reference Example 1 except for not using the V component, a gaseous mixture of propane, ammonia, air and nitrogen of the same composition as in Example 1 was supplied into a reactor at the same space velocity as in Example 1 to carry out the reaction at the temperature shown in Table 2. The results are shown in Table 2.

COMPARATIVE EXAMPLE 4

While using a catalyst of the atomic ratio shown in Table 2 prepared in the same manner as in Reference Example 1 except for not using the Mo component, a gaseous mixture of propane, ammonia, air and nitrogen of the same composition as in Example 1 was supplied into a reactor at the same space velocity as in Example 1 to carry out the reaction at the temperature shown in Table 2. The results are shown in Table 2.

From the comparison of Examples 1 to 4 and Comparative Examples 1 to 4, it is understood that as the component of the catalyst of the present invention, all of Mo, V, Te and Nb are the indispensable components for obtaining a high selectivity.

TABLE 2

| Comparative Example | Catalyst (atomic ratio) | Temperature (°C.) | Conversion of propane (%) | Selectivity of acrylonitrile (%) |
|---|---|---|---|---|
| 1 | $Mo_{1.0}V_{0.4}Te_{0.2}O_{4.4}$ | 464 | 7.6 | 2.0 |
| 2 | $Mo_{1.0}V_{0.4}Nb_{0.1}O_{4.25}$ | 417 | 34.2 | 10.5 |
| 3 | $Mo_{1.0}Nb_{0.1}Te_{0.2}O_{3.65}$ | 423 | 0.3 | trace |
| 4 | $V_{0.4}Nb_{0.1}Te_{0.2}O_{1.65}$ | 421 | 2.4 | trace |

EXAMPLE 5

After charging a reactor with 1 cc of the catalyst obtained in Reference Example 1, a gaseous mixture of propane, ammonia and nitrogen of the molar ratio of 1:1.2:14.9 was supplied to the reactor at the space velocity of 700 hr$^{-1}$ for 5 minutes to carry out the gas phase contact catalytic reaction at 401° C.

The conversion was 9.9 % and the selectivity was 76.3 %.

Although in this Example, the oxidation reaction of propane was carried out without supplying molecular oxygen, acrylonitrile was obtained at a high selectivity only through oxidation reaction by the oxygen atoms which existed in the catalyst.

EXAMPLES 6 and 7

While respectively using 0.5 cc of each of the two catalysts obtained in Reference Example 2 and supplying the gaseous mixture of propane, ammonia, air and nitrogen of the molar ratio of 1:1.2:7.6:7.3 at the space velocity of 1400 hr$^{-1}$ to a reactor, the gas phase contact catalytic reaction was carried out at 422° C.

The results are shown in Table 3.

TABLE 3

| Example | Catalyst (atomic ratio) | Temperature (°C.) | Conversion of propane (%) | Selectivity of acrylonitrile (%) |
|---|---|---|---|---|
| 6 | $Mo_{1.0}V_{0.4}Te_{0.3}Nb_{0.1}O_{4.85}$ | 423 | 20.2 | 60.9 |
| 7 | $Mo_{1.0}V_{0.4}Te_{0.4}Nb_{0.1}O_{5.05}$ | 424 | 15.2 | 52.7 |

EXAMPLES 8 to 10

After charging a reactor with 0.5 cc of the catalyst obtained in Reference Example 1, the gaseous mixture of isobutane, ammonia, air and nitrogen of a composition shown in Table 4 was supplied to the reactor at a space velocity of 1400 hr$^{-1}$ to carry out the gas phase contact catalytic reaction at 448° C. The results are shown in Table 4.

TABLE 4

| Example | Composition of gas (molar ratio) | | | | Conversion of isobutane (%) | Selectivity of methacrylonitrile (%) |
|---|---|---|---|---|---|---|
| | Isobutane | NH$_3$ | Air | N$_2$ | | |
| 8 | 1 | 1.2 | 7.6 | 7.3 | 15.2 | 22.4 |
| 9 | 1 | 1.2 | 5.1 | 9.8 | 11.0 | 42.7 |
| 10 | 1 | 1.2 | 2.7 | 12.2 | 6.0 | 41.6 |

What is claimed is:

1. A process for producing acrylonitrile or methacrylonitrile, which comprises subjecting propane or isobutane and ammonia to gas-phase contact catalytic oxidation reaction in the presence of a complex oxide solid catalyst consisting of molybdenum, vanadium, tellurium, niobium and oxygen, represented by the following formula:

$$Mo_{1.0}V_a Te_b Nb_c O_x$$

wherein a, b and c represent the atomic ratio of each of the elements to one atom of Mo, a being 0.01 to 1.0, b being 0.1 to 0.5 and c being 0.01 to 1.0, and x represents a number decided by a total number of valences of the metal elements, thereby converting said propane or isobutane to a corresponding mononitrile.

2. A process according to claim 1, wherein said gas-phase contact catalytic reaction is carried out in the presence of molecular oxygen.

* * * * *

UNITED STATES PATENT AND TRADEMARK OFFICE
CERTIFICATE OF CORRECTION

PATENT NO. : 5,049,692

DATED : September 17, 1991

INVENTOR(S) : Masakatsu Hatano et al.

It is certified that error appears in the above-identified patent and that said Letters Patent is hereby corrected as shown below:

On the title page:
 The second Priority data is incorrect, should be,

--Feb. 18, 1988 [JP]  Japan............63-33999--.

Signed and Sealed this

Second Day of March, 1993

Attest:

STEPHEN G. KUNIN

*Attesting Officer*      Acting Commissioner of Patents and Trademarks